(12) United States Patent
Chorghade et al.

(10) Patent No.: US 7,285,676 B2
(45) Date of Patent: Oct. 23, 2007

(54) SYNTHESIS OF CHIRAL 2-ALKYL AMINO ACIDS

(75) Inventors: Mukund S. Chorghade, Natick, MA (US); Mukund K. Gurjar, Pune Maharashtra (IN); Bhanu M. Chanda, Pune Maharashtra (IN)

(73) Assignee: Genzyme Corporation, Cambridge, MA (US)

( * ) Notice: Subject to any disclaimer, the term of this patent is extended or adjusted under 35 U.S.C. 154(b) by 207 days.

(21) Appl. No.: 11/085,824

(22) Filed: Mar. 21, 2005

(65) Prior Publication Data

US 2006/0069265 A1    Mar. 30, 2006

Related U.S. Application Data

(63) Continuation of application No. 10/439,313, filed on May 15, 2003, now Pat. No. 6,903,220.

(60) Provisional application No. 60/392,833, filed on Jun. 27, 2002, provisional application No. 60/381,012, filed on May 15, 2002, provisional application No. 60/381,021, filed on May 15, 2002, provisional application No. 60/380,894, filed on May 15, 2002, provisional application No. 60/380,910, filed on May 15, 2002, provisional application No. 60/380,880, filed on May 15, 2002, provisional application No. 60/381,017, filed on May 15, 2002, provisional application No. 60/380,895, filed on May 15, 2002, provisional application No. 60/380,903, filed on May 15, 2002, provisional application No. 60/381,013, filed on May 15, 2002, provisional application No. 60/380,878, filed on May 15, 2002, provisional application No. 60/380,909, filed on May 15, 2002.

(51) Int. Cl.
    C07C 323/52    (2006.01)
(52) U.S. Cl. .................................. 560/153; 562/557
(58) Field of Classification Search ................ 560/153; 562/557
    See application file for complete search history.

(56) References Cited

U.S. PATENT DOCUMENTS

| 4,406,905 | A | 9/1983 | Zähner et al. |
|---|---|---|---|
| 5,554,753 | A | 9/1996 | O'Donnell et al. |
| 5,840,739 | A | 11/1998 | Bergeron, Jr. |
| 5,872,259 | A | 2/1999 | Reuter |
| 5,929,232 | A | 7/1999 | Jacobsen et al. |
| 6,083,966 | A | 7/2000 | Bergeron, Jr. |
| 6,159,983 | A | 12/2000 | Bergeron, Jr. |
| 6,383,233 | B1 | 5/2002 | Reuter |
| 6,407,281 | B1 | 6/2002 | Ueda et al. |
| 6,428,583 | B1 | 8/2002 | Reuter |
| 6,521,652 | B1 | 2/2003 | Bergeron |
| 6,525,080 | B1 | 2/2003 | Bergeron |
| 6,559,315 | B1 | 5/2003 | Bergeron |
| 6,703,031 | B1 | 3/2004 | Iwasaki et al. |
| 6,765,109 | B1 | 7/2004 | Brown et al. |
| 6,794,515 | B2 | 9/2004 | Gimi et al. |
| 6,903,220 | B2 | 6/2005 | Chorghade et al. |
| 7,115,769 | B2 * | 10/2006 | Gimi et al. .................. 560/153 |
| 2003/0088105 | A1 | 5/2003 | Krich et al. |
| 2003/0220504 | A1 | 11/2003 | Chorghade et al. |
| 2003/0229231 | A1 | 12/2003 | Chorghade et al. |
| 2003/0236404 | A1 | 12/2003 | Gimi et al. |
| 2003/0236426 | A1 | 12/2003 | Chorghade et al. |
| 2003/0236434 | A1 | 12/2003 | Gimi et al. |
| 2003/0236435 | A1 | 12/2003 | Gimi et al. |
| 2004/0002613 | A1 | 1/2004 | Chorghade et al. |
| 2004/0006224 | A1 | 1/2004 | Chorghade et al. |
| 2004/0024224 | A1 | 2/2004 | Chorghade et al. |

FOREIGN PATENT DOCUMENTS

| DE | 20 20 866 A | 11/1971 |
|---|---|---|
| DE | 30 02 989 A1 | 7/1981 |
| EP | 1 302 467 A2 | 4/2003 |
| GB | 1 292 170 | 10/1972 |
| WO | WO 94/11367 | 5/1994 |
| WO | WO 97/36885 | 10/1997 |
| WO | WO 00/01670 | 1/2000 |
| WO | WO 00/12493 | 3/2000 |
| WO | WO 00/16763 | 3/2000 |

OTHER PUBLICATIONS

Ehrler, Juerg, and Farooq, Saleem, "Total Synthesis of Thiangazole," *Synlett*, 702-704 (1994).

(Continued)

*Primary Examiner*—Kamal A. Saeed
(74) *Attorney, Agent, or Firm*—Hamilton, Brook, Smith & Reynolds, P.C.

(57) ABSTRACT

Non-natural amino acids such as 2-alkylated amino acids allow for the synthesis of a wider variety of peptidal and non-peptidal pharmaceutically active agents. A method of preparing a 2-alkyl amino acid involves reacting cysteine (or a salt or an ester thereof) and an aryl carboxylic acid to form a thiazoline ring, stereospecifically alkylating the thiazoline ring, and hydrolyzing the thiazoline ring to obtain a 2-alkylcysteine (or related compound). The present invention also discloses a method of preparing a class of iron chelating agents related to desferrithiocin, all of which contain a thiazoline ring. In this method, an aryl nitrile or imidate is condensed with cysteine, a 2-alkyl cysteine, or a cysteine ester.

14 Claims, No Drawings

OTHER PUBLICATIONS

Kishore, V., et al., "Synthesis of α-Poly-[N$^\varepsilon$-(2-aryl-Δ$^2$-thiazoline-4-carbonyl)-L-lysines] With Antiviral Activity," *Indian Journal of Chemistry 15B*: 255-257 (1977).

Zamri, Adel, and Abdallah, Mohamed A., "An Improved Stereocontrolled Synthesis of Pyochelin, Siderophore of *Pseudomonas aeruginosa* and *Burkholderia cepacia*," *Tetrahedron 56*: 249-256 (2000).

Bergeron, R., et al., "DesazadesmethyIdesferrithiocin Analogues as Orally Effective Iron Chelators," *J. Med. Chem.*, 42:95-108 (1999).

Bergeron, R. et al., "The Desferrithiocin Pharmacophore," *J. Med. Chem.*, 37:1411-1417 (1994).

Bergeron, R. et al., "Effects of C-4 Stereochemistry and C-4 Hydroxylation on the Iron Clearing Efficiency and Toxicity of Desferrithiocin Analogues," *J. Med. Chem.*, 42:2432-2440 (1999).

Bergeron, R. et al., "Synthesis and Biological Evaluation of Naphthyldesferrithiocin Iron Chelators," *J. Med. Chem.*, 39:1575-1581 (1996).

Bergeron, R. et al., "Evaluation of Desferrithiocin and Its Synthetic Analogues as Orally Effective Iron Chelators," *J. Med. Chem.*, 34:2072-2078 (1991).

Bergeron, R. et al., "Evaluation of the Desferrithiocin Pharmacophore as a Vector for Hydroxamates," *J. Med. Chem.*, 42:2881-2886 (1999).

Bergeron, R. et al., "An Investigation of Desferrithiocin Metabolism," *J. Med. Chem.*, 37:2889-2895 (1994).

Bergeron, R. et al., "A Comparative Study of the Iron-Clearing Properties of Desferrithiocin Analogues with Desferrioxamine B in a *Cebus* Monkey Model," *Blood*, 81(8):2166-2173 (1993).

Bergeron, R. et al., "Pharmacokinetics of Orally Administered Desferrithiocin Analogs in *Cebus Apella* Primates," *Drug Metabolism and Disposition*, 27(12):1496-1498 (1999).

Mulqueen, G. C., et al., "Synthesis of the Thiazoline-based Siderophore (S)-Desferrithiocin," *Tetrahedron*, 49(24):5359-5364 (1993).

O'Donnell, M. J., et al., "α-Methyl Amino Acids by Catalytic Phase-Transfer Aklylations," *Tetrahedron Letters*, 23(41):4259-4262 (1982).

\* cited by examiner

SYNTHESIS OF CHIRAL 2-ALKYL AMINO ACIDS

RELATED APPLICATIONS

This application is a continuation of U.S. patent application Ser. No. 10/439,313 (now allowed as U.S. Pat. No. 6,903,220) which was filed on May 15, 2003. U.S. patent application Ser. No. 10/439,313 claims the benefit of U.S. Provisional Application Nos. 60/381,012, 60/381,021, 60/380,894, 60/380,910, 60/380,880, 60/381,017, 60/380,895, 60/380,903, 60/381,013, 60/380,878 and 60/380,909, all of which were filed May 15, 2002. U.S. patent application Ser. No. 10/439,313 also claims the benefit of U.S. Provisional Application No. 60/392,833, filed Jun. 27, 2002. The entire teachings of the above-referenced applications are incorporated herein by reference.

BACKGROUND OF THE INVENTION

Alpha-amino acids are useful starting materials in the synthesis of peptides, as well as non-peptidal, pharmaceutically active peptidomimetic agents. In order to enable the synthesis of a large number of compounds from an amino acid precursor, it is advantageous to have naturally occurring and non-naturally occurring amino acids. Non-naturally occurring amino acids typically differ from natural amino acids by their stereochemistry (e.g., enantiomers), by the addition of alkyl groups or other functionalities, or both. At this time, the enantiomers of naturally occurring amino acids are much more expensive than the naturally occurring amino acids. In addition, there are only a limited number of commercially available amino acids that are functionalized or alkylated at the alpha-carbon, and often syntheses involve the use of pyrophoric or otherwise hazardous reagents. Moreover, the syntheses are often difficult to scale up to a commercially useful quantity. Consequently, there is a need for new methodologies of producing such non-naturally occurring amino acids.

Non-naturally occurring amino acids of interest include the (R)— and (S)-isomers of 2-methylcysteine, which are used in the design of pharmaceutically active moieties. Several natural products derived from these isomers have been discovered in the past few years. These natural products include desferrithiocin, from *Streptomyces antibioticus*; as well as tantazole A, mirabazole C, and thiangazole, all from blue-green algae. These compounds have diverse biological activities ranging from iron chelation to murine solid tumor-selective cytotoxicity to inhibition of HIV-1 infection.

Desferrithiocin, deferiprone, and related compounds represent an advance in iron chelation therapy for subjects suffering from iron overload diseases. Present therapeutic agents such as desferroxamine require parenteral administration and have a very short half-life in the body, so that patient compliance and treatment cost are serious problems for subjects receiving long-term chelation therapy. Desferrithiocin and related compounds are effective when orally administered, thereby reducing patient compliance issues. Unfortunately, (S)-2-methylcysteine, which is a precursor to the more active forms of desferrithiocin and related compounds, remains a synthetic challenge. Therefore, there is a need for novel methods of producing 2-methylcysteine at a reasonable cost, and means of isolating the desired enantiomer.

SUMMARY OF THE INVENTION

The present invention includes a method of preparing a compound represented by Structural Formula (I):

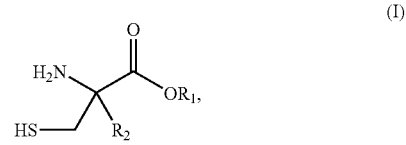

(I)

or salts thereof; wherein, $R_1$ is —H or a substituted or unsubstituted alkyl group; and $R_2$ is a substituted or unsubstituted alkyl group; comprising the steps of:

a.) reacting a compound represented by Structural Formula (II):

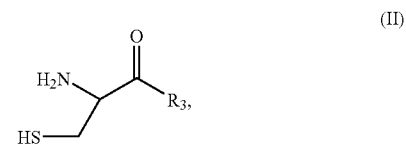

(II)

wherein $R_3$ is —OH, a substituted or unsubstituted alkyloxy group, or a halogen; with a substituted or unsubstituted aryl carboxylic acid, thereby forming a substituted thiazoline represented by Structural Formula (III):

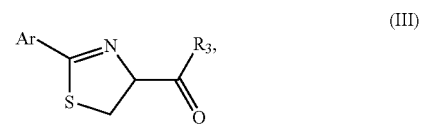

(III)

wherein Ar is a substituted or unsubstituted aryl group and $R_3$ is as defined above;

b.) reacting the substituted thiazoline with a substituted oxazolidinone represented by Structural Formula (IV):

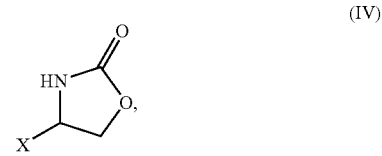

(IV)

wherein X is an aryl or an arylalkyl group, thereby forming a compound represented by Structural Formula (V):

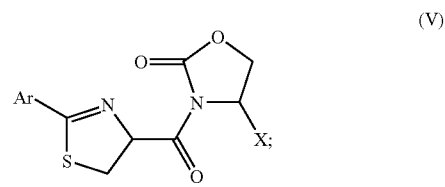

(V)

c.) alkylating the product of step (b.) with $R_2Y$, wherein $R_2$ is as defined above and Y is a leaving group; thereby forming a compound represented by Structural Formula (VI):

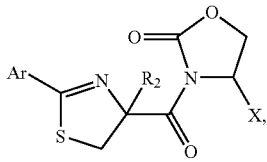

(VI)

wherein $R_2$ is as defined above; and d.) hydrolyzing the product of step (c.) (preferably an inorganic acid such as HCl, HBr or sulfuric acid), thereby forming the compound represented by Structural Formula (I).

In one embodiment, the present invention is a method of preparing a compound represented by Structural Formula (VII):

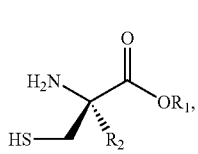

(VII)

or salts thereof, where $R_1$ is —H or a substituted or unsubstituted alkyl group; and $R_2$ is a substituted or unsubstituted alkyl group; comprising the steps of:

a) reacting a compound represented by Structural Formula (VIII):

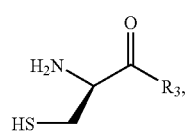

(VIII)

wherein $R_3$ is —OH, a substituted or unsubstituted alkyloxy group, or a halogen; with a substituted or unsubstituted aryl carboxylic acid, thereby forming a substituted thiazoline represented by Structural Formula (IX):

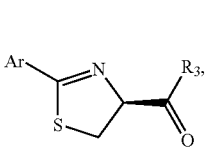

(IX)

wherein Ar is a substituted or unsubstituted aryl group and $R_3$ is as defined above;

b) reacting the substituted thiazoline with a substituted oxazolidinone represented by Structural Formula (X):

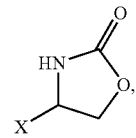

(X)

wherein X is an aryl or an arylalkyl group, thereby forming a compound represented by Structural Formula (XI):

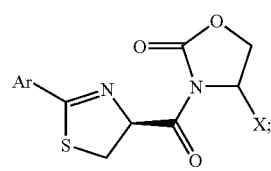

(XI)

c) alkylating the product of step (b.) with $R_2Y$, wherein $R_2$ is as defined above and Y is a leaving group; thereby forming a compound represented by Structural Formula (XII):

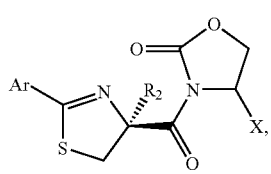

(XII)

wherein $R_2$ is as defined above; and d) hydrolyzing the product of step (c.), thereby forming the compound represented by Structural Formula (VII).

The present invention also includes method of preparing a compound represented by Structural Formula (XIII):

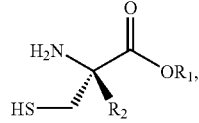

(XIII)

or salts thereof; where $R_1$ is —H or a substituted or unsubstituted alkyl group; and $R_2$ is a substituted or unsubstituted alkyl group; comprising the steps of:

a) reacting a compound represented by Structural Formula (XIV):

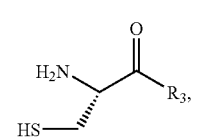

(XIV)

wherein $R_3$ is —OH, a substituted or unsubstituted alkyloxy group, or a halogen; with a substituted or unsubstituted aryl carboxylic acid, thereby forming a substituted thiazoline represented by Structural Formula (XV):

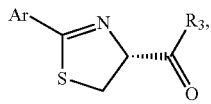

wherein Ar is a substituted or unsubstituted aryl group and $R_3$ is as defined above;

b) reacting the substituted thiazoline with a substituted oxazolidinone represented by Structural Formula (XVI):

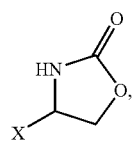

wherein X is an aryl or an arylalkyl group, thereby forming a compound represented by Structural Formula (XVII):

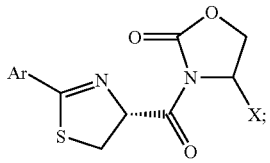

c) alkylating the product of step (b.) with $R_2Y$, wherein $R_2$ is as defined above and Y is a leaving group; thereby forming a compound represented by Structural Formula (XVIII):

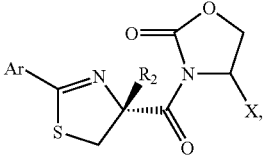

wherein $R_2$ is as defined above; and d) hydrolyzing the product of step (c.), thereby forming the compound represented by Structural Formula (XIII).

Preferably, the starting material for the above method is (S)-cysteine, and the product is (S)-2-methylcysteine methyl ester. Alternatively, the starting material for the above method is (R)-cysteine, and the product is (R)-2-methylcysteine methyl ester. The starting material for the above method can also be a mixture of (R)— and (S)-cysteine, such as the racemate, and the product is a mixture of (R)— and (S)-2-methylcysteine methyl ester.

In other embodiments of the invention, the stereochemistry at the 4-position of the thiazoline ring (i.e., where the amide is attached) may invert during the alkylation in step (c). This is dependent, for example, upon the ability of the amide group to exchange position with the electron pair formed after base deprotonates the thiazoline ring and upon the ability of the 2-oxazolidinone to selectively block the alkylating agent ($R_2Y$) from approaching a face of the thiazoline and prevent alkylation from occurring on that face. Under circumstances when stereochemical inversion occurs, to obtain an (S)-alkylated cysteine it may be advantageous to use (R)-cysteine or a derivative thereof as the starting material.

In another embodiment, the present invention is a method of preparing a compound represented by Structural Formula (VII):

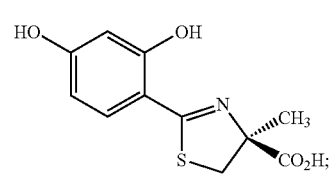

comprising the steps of:

a.) reacting a compound represented by Structural Formula (II):

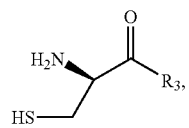

wherein $R_3$ is —OH, a substituted or unsubstituted alkyloxy group, or a halogen; with a substituted or unsubstituted aryl carboxylic acid, thereby forming a substituted thiazoline represented by Structural Formula (III):

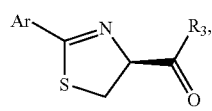

wherein Ar is a substituted or unsubstituted aryl group and $R_3$ is as defined above;

b.) reacting the substituted thiazoline with a substituted oxazolidinone represented by Structural Formula (IV):

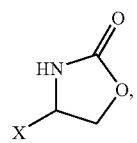

wherein X is an aryl or an arylalkyl group, thereby forming a compound represented by Structural Formula (V):

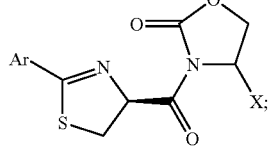

(V)

c.) alkylating the product of step (b.) with $R_2Y$, wherein $R_2$ is as defined above and Y is a leaving group; thereby forming a compound represented by Structural Formula (VI):

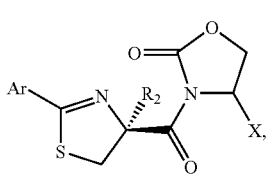

(VI)

wherein $R_2$ is as defined above; and d.) hydrolyzing the product of step (c.), thereby forming 2-methylcysteine or a salt thereof, and neutralizing the salt, if present; and e.) coupling (S)-2-methylcysteine with 2,4-dihydroxybenzonitrile, thereby forming the compound represented by Structural Formula (VII).

Alternative forms of the previous embodiment involve coupling 2-hydroxybenzonitrile and (S)-2-methylcysteine or a salt or an ester thereof. Similar syntheses can be conducted with other substituted benzonitriles or benzimidates.

Advantages of the present invention include the facile synthesis of a 2-alkyl cysteine, or a salt or ester thereof from cysteine, the acid chloride, or an ester thereof. 2-Methylcysteine prepared by the method of the present invention can be coupled to 2,4-dihydroxybenzonitrile to form 4'-hydroxy-desazadesferrithiocin, also referred to as 4,5-dihydro-2-(2, 4-dihydroxyphenyl)-4-methylthiazole-4(S)-carboxylic acid, an iron chelating agent.

DETAILED DESCRIPTION OF THE INVENTION

A useful and efficient method of preparing 2-alkyl cysteine and related compounds involves reacting cysteine (or a related compound, such as a cysteine alkyl ester or the acid chloride of cysteine) and an aryl carboxylic acid, to form a thiazoline intermediate. The thiazoline intermediate can be amidated with an oxazolidinone, and then stereospecifically alkylated. Upon hydrolysis of the thiazoline and the oxazolidinone, a 2-alkyl cysteine (or a related compound) is obtained.

The reaction of cysteine (or a related compound) with an aryl carboxylic acid can occur in a polar solvent, preferably a polar, protic solvent (e.g., methanol, ethanol, water, acetic acid, formic acid, isopropanol, propanol, dimethylformamide, N-ethylacetamide, formaldehyde diethyl acetal) with the addition of a base. Acceptable bases include alkali metal and alkaline earth metal salts, such as sodium hydroxide, sodium methoxide, sodium ethoxide, sodium carbonate, potassium hydroxide, potassium methoxide, potassium ethoxide, cesium carbonate, calcium carbonate, potassium carbonate, sodium hexamethyl disilazide, and potassium hexamethyl disilazide; and trialkylamines such as trimethylamine, triethylamine, and diisopropylethylamine. The aryl carboxylic acid is typically substituted or unsubstituted benzoic acid, but is preferably benzoic acid. The $R_3$ group of cysteine or a related compound can be a poor leaving group, such that peptide bond formation with amine-containing compounds is minimized.

The resultant 2-arylthiazoline-4-carboxylic acid can be amidated with a 4-aryl-2-oxazolidinone or a 4-arylalkyl-2-oxazolidinone. Preferably, the 4-arylalkyl-2-oxazolidinone is 4-benzyl-2-oxazolidinone. The 4-aryl-2-oxazolidone can have either an (R) or (S) configuration at the 4-position of the oxazolidinone ring, which is selected dependent in part upon the desired stereochemistry of the alkylated cysteine product. This amidation reaction is typically conducted in a polar solvent (e.g., acetonitrile, dimethylsulfoxide, dimethylformamide, acetone, hexamethylphosphoramide, methylene chloride, chloroform) in the presence of a catalytic amount of coupling or promoting agent, such as thionyl chloride, dicyclohexylcarbodiimide, diisopropylcarbodiimide, N,N-carbonyldiimidazole, $POCl_3$, $TiCl_4$, $SO_2ClF$, benzotriazol-1-yl diethyl phosphate, $Ti(O-butyl)_4$, N,N,N',N'-tetramethyl(succinimido)uranium tetrafluoroborate, 1,1'-carbonylbis(3-methylimidazolium)triflate, Lawesson's reagent, chlorosulfonyl isocyanate, $P_2I_4$, pyridinium salts with tributylamine, and a mixture of tributylphosphine and nitrosomethylbenzene.

The 2-aryl-thiazoline-4-carboxamide can be alkylated at the 4-position of the thiazoline ring by reacting it with base and an alkyating agent of the formula $R_2Y$, where $R_2$ and Y are as defined above. The alkylating agent is typically present in excess, such as about a 2-fold, 3-fold, 4-fold, 5-fold, or 10-fold excess. Preferably, $R_2$ is a substituted or unsubstituted C1-C4 alkyl group. Even more preferably, $R_2$ is methyl or benzyl. Y is preferably a halide, such as iodide, chloride, or bromide. Acceptable bases include lithium diisopropylamide (LDA), lithium diisopropylamide, lithium N-isopropyl-N-cyclohexylamide, potassium t-butoxide, sodium t-butoxide, sodium amide, potassium amide, sodium hydride, and potassium hydride. Titanium(IV) chloride or tin(IV) chloride can also be present in the reaction mixture. When titanium chloride is present, the reaction is carried out under nitrogen and in a water-free solvent. The reaction temperature is often about −25° C. to about 0° C. Acceptable solvents are polar, aprotic solvents such as acetone, acetonitrile, dimethylformamide, dioxane, ethyl acetate, ethyl ether, hexamethylphosphoramide, tetrahydrofuran, and 1,2-dimethoxyethane.

After alkylation, the 4-alkyl-2-arylthiazoline-4-carboxamide is generally hydrolyzed. Typically, hydrolysis involves reacting the 4-alkyl-2-arylthiazoline-4-carboxamide with an appropriate amount of base in a polar, protic solvent. Preferred bases include alkali and alkaline earth metal salts such as lithium hydroxide, potassium carbonate, calcium carbonate, and cesium carbonate. Preferred solvents include C1-C4 alcohols such as methanol, ethanol, propanol, isopropanol, butanol, isobutanol, and t-butanol. Methanol is an especially preferred solvent. In this reaction, the solvent is also a reactant, such that when an alcohol of formula $R_1OH$ is the solvent, $R_1O$ becomes part of the newly-formed ester. For example, when methanol is the solvent, the product is a 2-alkylcysteine methyl ester. The ester moiety can be hydrolyzed by reacting the cysteine ester with a sufficient quantity of acid or base to remove the methoxy group. The acid or base used for hydrolysis preferably does not react with or cleave, except to form a salt, other moieties of the 2-alkylcysteine.

Chiral amino acid products, either enantiomers or diastereomers, of the above syntheses can be purified by an additional resolving step. Typically, amino acids are resolved by forming a diastereomeric salt with an amino acid and a chiral amine. Suitable chiral amines include arylalkylamines such as (R)-1-phenylethylamine, (S)-1-phenylethylamine, (R)-1-tolylethylamine, (S)-1-tolylethylamine, (R)-1-phenylpropylamine, (S)-1-propylamine, (R)-1-tolylpropylamine, and (S)-1-tolylpropylamine. Resolution of chiral compounds using diastereomeric salts is further described in *CRC Handbook of Optical Resolutions via Diastereomeric Salt Formation* by David Kozma (CRC Press, 2001), which is incorporated herein by reference in its entirety.

Alternatively, 2-alkyl amino acids and functionalized derivatives thereof (e.g., esters) can be purified by emulsion crystallization, as described in U.S. Pat. Nos. 5,872,259, 6,383,233 and 6,428,583, which are incorporated herein by reference. Briefly, emulsion crystallization is a process for separating a desired substance from an aggregate mixture. The process involves forming a three phase system, the first phase comprising the aggregate mixture, the second phase being liquid and comprising a transport phase, and the third phase comprising a surface upon which the desired substance can crystallize. A chemical potential exists for crystal growth of the desired substance in the third phase of the system, thereby creating a flow of the desired substance from the first phase through the second phase to the third phase, where the desired substance crystallizes and whereby an equilibrium of the activities of the remaining substances in the aggregate mixture is maintained between the first phase and the second phase.

In one example of emulsion crystallization, a solution of the racemic mixture is supersaturated (by either cooling, adding a solvent in which one or more components are sparingly soluble or by evaporation of the solution). Ultrasonication eventually helps the process of forming an emulsion. The mixture is then seeded with crystals of the desired, optically active acid along with an additional quantity of surfactant and an anti-foaming agent. The desired product usually crystallizes out and can be separated by filtration. Further details of emulsion crystallization for an amino acid derivative can be found in Example 2.

Once the 2-alkyl amino acids or functionalized derivatives have been resolved, the desired isomer can be isolated. Typically, a (S)-2-amino acid, a salt, or an ester thereof is isolated. Preferably, (S)-2-methylcysteine or (S)-2-methylcysteine methyl ester is isolated.

Cysteine, a 2-alkylcysteine such as (S)-2-methylcysteine, or a cysteine alkyl ester can be coupled to a substituted or unsubstituted aryl nitrile such as a substituted or unsubstituted benzonitrile. Preferably, the substituents on benzonitrile will not interfere with the coupling reaction. In a preferred embodiment, (S)-2-methylcysteine is coupled to 2,4-dihydroxybenzonitrile to form 4,5-dihydro-2-(2,4-dihydroxyphenyl)-4-methylthiazole-4(S)-carboxylic acid (also known as 4'-hydroxydesazadesferrithiocin).

Typically, coupling of cysteine, a 2-alkylcysteine, or a cysteine alkyl ester and a substituted or unsubstituted benzonitrile includes converting the benzonitrile into a benzimidate. The benzimidate can be formed, for example, by reacting the benzonitrile with an alcohol such as methanol, ethanol, n-propanol, or isopropanol in the presence of an acid such as hydrochloric acid. Alternatively, cysteine or a related compound can be coupled directly with a benzimidate. The benzimidate is then reacted with the cysteine (or related compound) under basic conditions. Acceptable bases include trimethylamine, triethylamine, triphenylamine, dimethylamine, diethylamine, diphenylamine, diisopropylamine, diisopropylethylamine, 1,4-diazabicyclo[2.2.2]octane (DABCO), 1,5-diazabicyclo[4.3.0]non-5-ene (DBN), and the like. The reaction between the benzimidate and the cysteine results in the thiazoline (or 4,5-dihydrothiazole) containing product. When forming the benzimidate from a hydroxylated benzonitrile (e.g., 2,4-dihydroxybenzonitrile), the hydroxyl groups are advantageously protected (e.g., with a substituted or unsubstituted alkyl or arylalkyl group such as a benzyl group). The protecting groups are subsequently cleaved, typically by catalytic hydrogenation.

The methods of the claimed invention can be used to manufacture other related desferrithiocin analogs and derivatives. Examples of such analogs include those described in U.S. Pat. Nos. 5,840,739, 6,083,966, 6,159,983, 6,521,652 and 6,525,080 to Raymond J. Bergeron, Jr., the contents of which are incorporated herein by reference. Additional examples can be found in PCT/US93/10936, PCT/US97/04666, and PCT/US99/19691, the contents of which are incorporated by reference.

Suitable benzonitriles and benzimidates for use in the above coupling reaction can be synthesized by methods described in U.S. application Ser. Nos. 60/381,013, 60/380,878 and 60/380,909, all filed May 15, 2002, the entire teachings of which are incorporated herein by reference.

An alkyl group is a hydrocarbon in a molecule that is bonded to one other group in the molecule through a single covalent bond from one of its carbon atoms. Alkyl groups can be cyclic or acyclic, branched or unbranched, and saturated or unsaturated. Typically, an alkyl group has one to about 24 carbons atoms, or one to about 12 carbon atoms. Lower alkyl groups have one to four carbon atoms and include methyl, ethyl, n-propyl, iso-propyl, n-butyl, sec-butyl and tert-butyl.

Aromatic or aryl groups include carbocyclic aromatic groups such as phenyl, p-tolyl, 1-naphthyl, 2-naphthyl, 1-anthracyl and 2-anthracyl. Aryl groups also include heteroaryl groups include N-imidazolyl, 2-imidazole, 2-thienyl, 3-thienyl, 2-furanyl, 3-furanyl, 2-pyridyl, 3-pyridyl, 4-pyridyl, 2-pyrimidyl, 4-pyrimidyl, 2-pyranyl, 3-pyranyl, 3-pyrazolyl, 4-pyrazolyl, 5-pyrazolyl, 2-pyrazinyl, 2-thiazolyl, 4-thiazolyl, 5-thiazolyl, 2-oxazolyl, 4-oxazolyl and 5-oxazolyl.

Aryl groups also include fused polycyclic aromatic ring systems in which a carbocyclic, alicyclic, or aromatic ring or heteroaryl ring is fused to one or more other heteroaryl or aryl rings. Examples include 2-benzothienyl, 3-benzothienyl, 2-benzofuranyl, 3-benzofuranyl, 2-indolyl, 3-indolyl, 2-quinolinyl, 3-quinolinyl, 2-benzothiazole, 2-benzooxazole, 2-benzimidazole, 2-quinolinyl, 3-quinolinyl, 1-isoquinolinyl, 3-quinolinyl, 1-isoindolyl and 3-isoindolyl.

Suitable substituents for alkyl groups include —OH, halogen (—Br, —Cl, —I and —F), —O(R'), —O—CO—(R'), —CN, —NO$_2$, —COOH, =O, —NH$_2$, —NH(R'), —N(R')$_2$, —COO(R'), —CONH$_2$, —CONH(R'), —CON(R')$_2$, —SH, —S(R'), and guanidine. Each R' is independently an alkyl group or an aryl group. Alkyl groups can additionally be substituted by a aryl group (e.g. an alkyl group can be substituted with an aromatic group to form an arylalkyl group). A substituted alkyl group can have more than one substituent.

Suitable substituents for aryl groups include —OH, halogen (—Br, —Cl, —I and —F), —O(R'), —O—CO—(R'), —CN, —NO$_2$, —COOH, =O, —NH$_2$, —NH(R'), —N(R')$_2$, —COO(R'), —CONH$_2$, —CONH(R'), —CON(R')$_2$, —SH, —S(R'), and guanidine. Each R' is independently an alkyl group or an aryl group. Aryl groups can additionally be substituted by an alkyl or cycloaliphatic group (e.g. an aryl group can be substituted with an alkyl group to form an alkylaryl group such as tolyl). A substituted aryl group can have more than one substituent.

Leaving groups are typically weak bases. Suitable leaving groups include halogen, tosyl, triflyl, brosyl, p-nitrophenyl, 2,4-dinitrophenyl, and mesyl groups. Halogens include bromine, chlorine, and iodine.

Also included in the present invention are salts of the disclosed 2-alkylcysteines. For example, cysteines can also be present in the anionic, or conjugate base, form, in combination with a cation. Suitable cations include alkali metal ions, such as sodium and potassium ions, alkaline earth ions, such as calcium and magnesium ions, and unsubstituted and substituted (primary, secondary, tertiary and quaternary) ammonium ions. Suitable cations also include transition metal ions such as manganese, copper, nickel, iron, cobalt, and zinc. Basic groups such as amines can also be protonated with a counter anion, such as hydroxide, halogens (chloride, bromide, and iodide), acetate, formate, citrate, ascorbate, sulfate or phosphate.

EXAMPLE 1

(S)-Cysteine is reacted with benzoic acid to form 2-phenylthiazoline-4-carboxylic acid. 2-Phenylthiazoline-4-carboxylic acid is amidated with 4-benzyloxazolidone. The amidated 2-phenylthiazoline-4-carboxylic acid is alkylated with methyl iodide in the presence of TiCl$_4$ and lithium diisopropylamide. The alkylated species is hydrolyzed by lithium hydroxide in methanol to obtain (S)-2-methylcysteine methyl ester.

EXAMPLE 2

All compounds were used without further purification. The surfactants Rhodafac RE 610 and Soprophor FL were obtained from Rhône-Poulenc, Surfynol 465 from Air Products, Synperonic NP 10 from ICI and sodium lauryl sulfate from Fluka. For agitation a shaking machine was used (Buhler K L Tuttlingen). Purities of the resulting crystals were measured by using a PolarMonitor polarimeter (IBZ Hannover). Ethanol was used as the solvent. The total crystal quantity was dissolved in a 1 mL cell at 20° C.)

45 mg of (R,R)- and (S,S)-amino acid derivatives were dissolved in 1 ml of a mixture of 20% v/v 2-hexanol, 12% v/v Rhodafac RE 610, 6% v/v Soprophor FL and 62% v/v water by heating to 80° C. in a 5 mL vial. After the organic derivative was completely dissolved the microemulsion was cooled down to room temperature and agitated using a shaking machine (420 rpm). During two hours no spontaneous crystallization was observed. The mixture was then seeded with two drops of a dilute, finely ground suspension of pure (S,S)-(−) amino acid or its ester crystals grown under similar conditions. After 2 hours of agitation the resulting crystals were filtered off, washed with water and dried in a gentle nitrogen stream.

EXAMPLE 3

35 mg of R- and S-4,5-dihydro-2-(2,4-dihydroxyphenyl)-4-methylthiazole-4-carboxylic acid were dissolved in 1 ml of a mixture of 9% N-methyl-pyrrolidone, 9% v/v 2-hexanol, 10% v/v Rhodafac RE 610, 5% v/v Soprophor FL and 68% v/v water by heating to 50° C. in a 5 mL vial. After the product was completely dissolved, the microemulsion was cooled down to room temperature and agitated with a shaking machine (350 rpm). During two hours, no spontaneous crystallisation was observed. The mixture was then seeded with two drops of a dilute, finely ground suspension of pure S-product crystals grown under similar conditions. After two hours of shaking, the resulting crystals were filtered off, washed with water and dried in a gentle nitrogen stream. The procedure yielded 5.4 mg (15.4%) of colorless crystals, with a greater than 90% purity of the S entantiomer.

EXAMPLE 4

4.00 g (S)-2-methylcysteine hydrochloride (23.3 mmol, 1.0 meq) and 3.14 g 2,4-dihydroxy benzonitrile (23.3 mmol, 1.0 meq) were suspended in 40 mL ethanol. After degassing this mixture with nitrogen (30 min) 4.95 g triethylamine (6.8 mL, 48.9 mmol, 2.05 meq) were added. The obtained suspension was heated under reflux in an atmosphere of nitrogen for 20 hours and then cooled to room temperature. From this suspension ethanol was evaporated under reduced pressure until an oil (20% of the initial volume) was obtained. This oil was dissolved in 50 mL water. The solution was adjusted to pH 7.5 with 1.20 ml 20% KOH and was extracted two times each with 20 mL methyl t-butyl ether (MTBE). The aqueous layer was separated, adjusted with 20% KOH to pH 11 and again extracted two times each with 20 mL MTBE. After separating the aqueous layer the pH was set with concentrated HCl to 7.5 and traces of MTBE were distilled off. Then the aqueous solution was acidified with 1.50 ml concentrated HCl to pH 1.5. The product precipitated. This suspension was stirred at 4° C. for 1 hour. Then the precipitate was filtered, washed two times each with 10 mL water (5° C.) and dried at 45° C. under vacuum. The reaction yielded 5.17 g (87.6%) of crude 4,5-dihydro-2-(2,4-dihydroxyphenyl)-4-methylthiazole-4(S)-carboxylic acid product. $^1$H-NMR showed no significant impurity.

EXAMPLE 5

2,4-Dibenzyloxybenzonitrile (0.121 mol) was dissolved in 5.85 g (0.127 mol) ethanol and 19.4 ml 1,2-dimethoxyethane in a double walled reactor. This solution was cooled to −5° C., stirred and saturated with dry HCl gas over 5 hours at 0-3° C. The reaction mixture was stirred overnight at 2-4° C. under nitrogen. During this time, a product crystallized. The white crystals were filtered off, washed with 1,2-dimethoxyethane (5° C., three times each with 13 ml) and dried. A total of 30 of the protected ethyl benzimidate was isolated (Yield 88.4%, purity 98.9%).

The protected ethyl benzimidate described above was dissolved in methanol to generate a 10% solution and was catalytically hydrogenated at room temperature using 5% Pd/C as a catalyst. The reaction was completed after 8 hours. The solution was filtered and the solvent evaporated to yield the deprotected product as an orange-yellow solid. The reaction yielded 19.6 g (94%) of product.

In contrast, the formation of the imidate with 2,4 dihydroxybenzonitrile was a low yielding process, generating the desired product in only 20% yield and with less than desired purity.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of preparing a compound represented by Structural Formula (I):

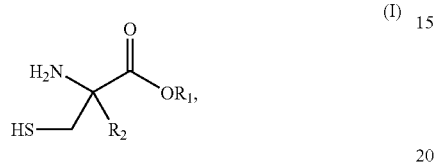

or salts thereof;

wherein, $R_1$ is —H or a substituted or unsubstituted alkyl group; and $R_2$ is a substituted or unsubstituted C1-C4 alkyl group; comprising the steps of:

a) reacting a compound represented by Structural Formula (II):

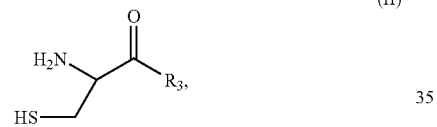

wherein $R_3$ is —OH, a substituted or unsubstituted alkyloxy group, or a halogen; with a substituted or unsubstituted benzoic acid, thereby forming a substituted thiazoline represented by Structural Formula (III):

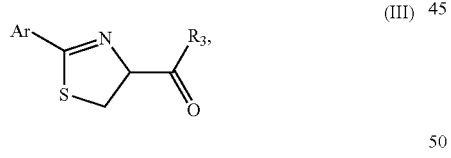

wherein Ar is a substituted or unsubstituted phenyl group and $R_3$ is as defined above;

b) reacting the substituted thiazoline with a substituted oxazolidinone represented by Structural Formula (IV):

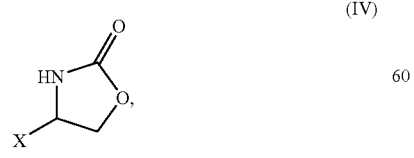

wherein X is an aryl or an arylalkyl group, thereby forming a compound represented by Structural Formula (V):

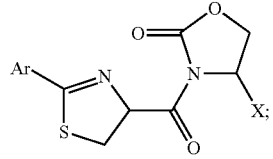

c) alkylating the product of step (b) with $R_2Y$ in the presence of a base in a polar, aprotic solvent, wherein $R_2$ is as defined above and Y is a leaving group; thereby forming a compound represented by Structural Formula (VI):

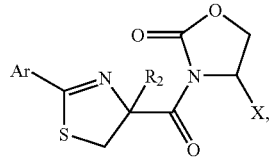

wherein $R_2$ is as defined above; and d) hydrolyzing the product of step (c), thereby forming the compound represented by Structural Formula (I).

2. The method of claim 1, wherein $R_1$ is a C1-C4 alkyl group.

3. The method of claim 2, wherein step (d) comprises reacting the product of step (c) with base and $R_1OH$, wherein $R_1$ is as defined above.

4. The method of claim 1, wherein X is benzyl.

5. The method of claim 1, wherein $R_2$ is methyl.

6. The method of claim 5, wherein $R_1$ is methyl.

7. The method of claim 6, wherein $R_3$ is —OH.

8. The method of claim 6, wherein the enantiomers of the product of step (d) are resolved.

9. The method of claim 8, wherein (S)-2-methylcysteine is isolated from the enantiomers.

10. A method of preparing a compound represented by Structural Formula (VII):

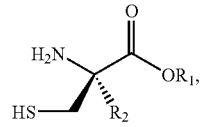

or salts thereof;

wherein, $R_1$ is —H or a substituted or unsubstituted alkyl group; and $R_2$ is a substituted or unsubstituted C1-C4 alkyl group; comprising the steps of:

a) reacting a compound represented by Structural Formula (VIII):

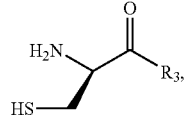

wherein R₃ is —OH, a substituted or unsubstituted alkyloxy group, or a halogen; with a substituted or unsubstituted benzoic acid, thereby forming a substituted thiazoline represented by Structural Formula (IX):

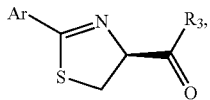
(IX)

wherein Ar is a substituted or unsubstituted phenyl group and R₃ is as defined above;

b) reacting the substituted thiazoline with a substituted oxazolidinone represented by Structural Formula (X):

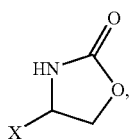
(X)

wherein X is an aryl or an arylalkyl group, thereby forming a compound represented by Structural Formula (XI):

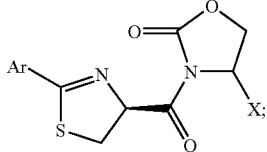
(XI)

c) alkylating the product of step (b) with R₂Y in the presence of a base in a polar, aprotic solvent, wherein R₂ is as defined above and Y is a leaving group; thereby forming a compound represented by Structural Formula (XII):

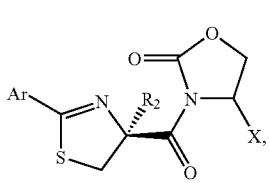
(XII)

wherein R₂ is as defined above; and d) hydrolyzing the product of step (c), thereby forming the compound represented by Structural Formula (VII).

11. The method of claim 10, wherein step (d) comprises reacting the product of step (c) with base and R₁ OH, wherein R₁ is as defined above.

12. The method of claim 10, wherein X is benzyl.

13. The method of claim 10, wherein R₂ is methyl.

14. The method of claim 13, wherein R₁ is methyl.

* * * * *